United States Patent [19]

Kodama et al.

[11] Patent Number: 4,782,168
[45] Date of Patent: Nov. 1, 1988

[54] 2,3-DIHYDRO-2,3,5-TRIMETHYL-4H-PYRAN-4-ONE DERIVATIVE AND SEX ATTRACTANT FOR DRUGSTORE BEETLES

[75] Inventors: Hisashi Kodama, Kawasaki; Keiko Mochizuki, Yokohama; Masahiro Kohno, Sagamihara; Akio Ohnishi, Yokohama; Mikio Ono, Fussa, all of Japan

[73] Assignees: Japan Tobacco, Inc.; Fuji Flavor Co., Ltd., both of Tokyo, Japan

[21] Appl. No.: 844,598

[22] Filed: Mar. 27, 1986

[30] Foreign Application Priority Data

Mar. 27, 1985 [JP] Japan .................................. 60-62337
Feb. 26, 1986 [JP] Japan .................................. 61-39155

[51] Int. Cl.⁴ .......................................... C07D 309/30
[52] U.S. Cl. .................................... 549/416; 549/420; 549/423
[58] Field of Search ...................... 549/420, 423, 416; 514/460

[56] References Cited

FOREIGN PATENT DOCUMENTS 2947422 6/1981 Fed. Rep. of Germany .
59-112981 6/1984 Japan .

OTHER PUBLICATIONS

Chemical Abstracts, vol. 95, 115,119a (1981).
Chemical Abstracts, vol. 99, 194,6638 (1983).

*Primary Examiner*—Nicky Chan
*Attorney, Agent, or Firm*—Nixon & Vanderhye

[57] ABSTRACT

A 2,3-dihydro-2,3,5-trimethyl-4H-pyran-4-one derivative represented by general formula:

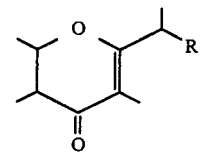

where R is

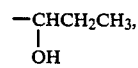

—CH(OCH₃)₂, —CH(OC₂H₅)₂, —CHO, —CH₂OH, —CH=CH₂, =CHCH₂CH₃, —CH=CHCH₃ or

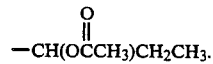

The derivative is useful as a sex attractant for drugstore beetles.

10 Claims, No Drawings

2,3-DIHYDRO-2,3,5-TRIMETHYL-4H-PYRAN-4-ONE DERIVATIVE AND SEX ATTRACTANT FOR DRUGSTORE BEETLES

BACKGROUND OF THE INVENTION

1. Field of the Invention

The present invention relates to a novel compound, 2,3-dihydro-2,3,5-trimethyl-4H-pyran-4-one derivative, and a sex attractant for drugstore beetles. 2. Description of the Prior Art Drugstore beetles (*Stegobium paniceum* Linne) are distributed worldwide and eat various substances including books and fibers and foodstuffs such as feeds, breads, or biscuits. Drugstore beetles also prefer herbs including medicinal carrots from which their name is derived, and are pests for stuffs stored in drug or food factories. Such indoor insects are closely associated with our daily life. For this reason, many safety measures must be taken in pest control of these worms and many pest control methods or drugs used for other types of insect cannot often be used. For example, in a specific type of warehouse, a fumigant having a strong toxicity such as hydrogen phosphide or methyl bromide is used as an insecticide for drugstore beetles. However, for the same purpose, only a DDVP drug can be used in factor working sites or warehouses in which people are expected to be exposed to such a drug frequently. However, the DDVP drug i.e., dimethyl 2,2-dichlorovinyl phosphate, does not have residual and permeating effects; it can kill adult drugstore beetles in an area in which they are easily exposed to the drug but it cannot kill adult drugstore beetles, or their eggs, larvae or pupas in concealed corners or the like. Thus, the DDVP requires frequent applicaton. Even if adult drugstore beetles are temporarily killed to a low population, emergence of remaining pupas may result in recovery of the original adult worm population within a short period of time. This presents a problem of frequent application of an insecticide and may be bad for health.

Many studies are recently made for attraction pest control using an insect sex pheromone or for pest control by disturbing communication between different sexes. In general, the mating behavior of insects is controlled by a very small amount of a scent-emitting substance secreted by insects themselves (normally female insects). An adult female insect emits a volatile material into the air, and an adult male insect flies or walks to the female insect emitting the volatile material. The male insect finds the female insect and becomes sexually excited so that the two insects engage in copulatory behavior. The scent-emitting substance from an adult female insect is generally called a sex pheromone or a sex attractant and is an important substance which controls the mating behavior of insects. Therefore, it is possible to attract and exterminate male insects at a selected location or to disturb normal mating behavior of adult male insects, thereby performing pest control. Further, when pests are attracted and exterminated using a sex pheromone and their occurrence is determined, need and timing for application of an insecticide can be determined and an insecticide will not be wasted.

SUMMARY OF THE INVENTION

It is an object of the present invention to provide a novel substance which can be used as a sex pheromone for drugstore beetles.

It is another object of the present invention to provide a sex attractant for drugstore beetles.

According to an aspect of the present invention, there is provided a 2,3-dihydro-2,3,5-trimethyl-4H-pyran-4-one derivative represented by the general formula:

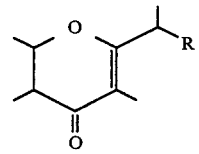

where R is

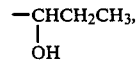

$-CH(OCH_3)_2$, $-CH(OC_2H_5)_2$, $-CHO$, $-CH_2OH$, $-CH=CH_2$, $=CHCH_2CH_3$, $-CH=CHCH_3$, or

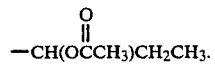

According to a second aspect of the present invention, there is provided a sex attractant for drugstore beetles, comprising the derivative of the invention.

DETAILED DESCRIPTION OF THE PREFERRED EMBODIMENTS

As described above, the compound according to the present invention is a 2,3-dihydro-2,3,5-trimethyl-4H-pyran-4-one derivative represented by general formula:

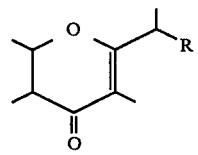

(I)

In Formula (I), R denotes

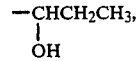

$-CH(OCH_3)_2$, $-CH(OC_2H_5)_2$, $-CHO$, $-CH_2OH$, $-CH=CH_2$, $=CHCH_2CH_3$, $-CH=CHCH_3$, or

The compound of the present invention can be obtained as follows.

(A) Preparation of 2,3-dihydro-2,3,5-trimethyl-6-(1-methyl-2-hydroxybutyl-4H-pyran-4-one or stegobiol {compound wherein R is hydroxypropyl group

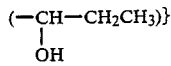

As will be described in detail in Example 1 to be described later, stegobiol can be extracted from drugstore beetles in the following manner. Adult female drugstore beetles are subjected to extraction with hexane. The extract is subjected to column chromatography (a final solvent is, e.g., ethyl ether), and then subjected to high-performance liquid chromatography (a solvent is, e.g., a mixture of hexane and tetrahydrofuran).

Stegobiol can also be synthesized by allowing sodium borohydride to react with 2,3-dihydro-2,3-5-trimethyl-6-(1-methyl-2-oxobutyl)-4H-pyran-4-one(stegobinone), thereby reducing stegobinone. Reduction is performed in an organic solvent such as ethyl ether or tetrahydrofuran (the latter is preferred) and at a temperature not higher than room temperature using about 0.25 to 0.5 moles (normally about 0.5 moles) of sodium borohydride per mole of stegobinone. The reduction time is normally 1 to 5 hours. This reaction yields various stereoisomers of stegobiol (i.e., diastereoisomers). Any of these stereoisomers is effective as a sex attractant and belongs to the scope of the present invention. Stegobinone is relatively unstable under alkaline conditions. Therefore, it is preferred to use a neutral metal borohydride, such as magnesium borohydride, instead of sodium borohydride in the reduction. The use of the neutral metal borohydride results in a higher yield of stegobiol.

The stegobinone can be manufactured by a method described in Japanese Patent Disclosure No. 59-112981.

(B) Preparation of 2,3-dihydro-2,3,5-trimethyl-6-(2-methyl-1,1-dimethoxyethyl)-4H-pyran-4-one {compound wherein R is dimethoxymethyl group (—CH(OCH₃)₂)}

This compound (to be referred to as compound (1) hereinafter) can be prepared by reacting 2,3-dihydro-2,3,5-trimethyl-6-ethyl-4H-pyran-4-one with methyl orthoformate in the presence of boron trifluoride and acetic anhydride. Acetic anhydride and methyl orthoformate are used in amounts of 1 to 3 moles, respectively, per mole of 2,3-dihydro-2,3,5-trimethyl-6-ethyl-4H-pyran-4-one. Boron trifluoride is used in an amount of 1/10 to 1 moles per mole of 2,3-dihydro-2,3,5-trimethyl-6-ethyl-4H-pyran-4-one. The reaction is performed at −10° C. to +30° C. for 2 to 10 hours.

(C) Preparation of 2,3-dihydro-2,3,5-trimethyl-6-(2-methyl-1,1-diethoxyethyl)-4H-pyran-4-on {compound wherein R is diethoxymethyl group (—CH(OC₂H₅)₂)}

This compound (to be referred to as compound (2) hereinafter) is prepared by performing the same reaction as in (A) above except that ethyl orthoformate is used in place of methyl orthoformate.

(D) Preparation of 2,3-dihydro-2,3,5-trimethyl-6-(2-methyl-1-oxoethyl)-4H-pyran-4-one {compound wherein R is aldehyde group (—CHO)}

This compound (to be referred to as compound (3) hereinafter) is prepared by performing hydrolysis of compound (1) with hydrochloric acid at 10° to 70° C. in acetonitrile. The hydrochloric acid having a concentration of 1 to 20% is used. The reaction time is 1 to 10 hours.

(E) Preparation of 2,3-dihydro-2,3,5-trimethyl-6-(2-methyl-1-hydroxyethyl)-4H-pyran-4-one {compound wherein R is hydroxymethyl group (—CH₂OH)}

This compound (to be referred to as compound (4) hereinafter) is prepared by reducing compound (3). The reducing agent can be zinc chloride-sodium borohydride (which form zinc borohydride) or the like. The reducing agent is added in an amount of 0.5 to 4 moles per mole of compound (3) and the reaction is performed at 0° to 30° C. for 1 to 10 hours.

(F) Preparation of 2,3-dihydro-2,3,5-trimethyl-6-(3-methyl-1-propenyl)-4H-pyran-4-one {compound wherein R is vinyl group (—CH=CH₂)}

This compound (to be referred to as compound (5) hereinafter) is prepared by suspending methyltriphenylphosphonium iodide in ether, cooling the suspension to −60° C. to +10° C., dripping a hexane solution of butyl lithium to the suspension, and dripping compound (3) to the mixture.

Methyltriphenylphosphonium iodide and butyl lithium are used in amounts of 1 to 3 moles, respectively, per mole of compound (3), and the reaction is performed for 1 to 5 hours.

(G) Preparation of 2,3-dihydro-2,3,5-trimethyl-6-(1-methyl-1-butenyl)-4H-pyran-4-one {compound wherein R is 1-propenyl group (=CHCH₂CH₃)}

This compound (to be referred to as compound (6) hereinafter) is prepared by reacting 2,3-dihydro-2,3,5-trimethyl-6-(2-methyl-2-bromo-1-oxoethyl)-4H-pyran-4-one sequentially with ethylmagnesium bromide and magnesium in an organic solvent such as diethyl ether or the like. Ethylmagnesium bromide and magnesium are used in amounts of 1 to 3 moles, respectively, per mole of 2,3-dihydro-2,3,5-trimethyl-6-(2-methyl-2-bromo-1-oxoethyl)-4H-pyran-4-one. The reaction is performed at 5° to 30° C. for 2 to 10 hours.

(H) Preparation of 2,3-dihydro-2,3,5-trimethyl-6-(1-methyl-2-butenyl)-4H-pyran-4-one {compound wherein R is propenyl group (—CH=CHCH₃)}

This compound (to be referred to as compound (7) hereinafter) is prepared by the same reaction as in (E) above except that ethyltriphenylphosphonium iodide is used in place of methyltriphenylphosphonium.

(I) Preparation of 2,3-dihydro-2,3,5-trimethyl-6-(1-methyl-2-acetoxy)-4H-pyran-4-one {compound wherein R is 1-acetoxypropyl group

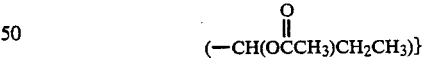

This compound (to be referred to as compound (8) hereinafter) is prepared by acetylating the hydroxyl group of stegobiol. The acetylation agent can be acetyl chloride or the like. The amount of an acetylation agent is 1 to 3 moles per mole of stegobiol. The acetylation is performed at 0° to 50° C. for 2 to 20 hours.

The compounds of the present invention described above can be directly used as sex attractants. However, a compound of the present invention is conveniently mixed in an amount of about 1 to 30 mg per gram of a carrier such as polypropylene powder and/or pulp powder, and pelletized. The resultant pellet is left in an open atmosphere.

Drugstore beetles occur in April to October in Japan and the sex attractant according to the present invention can be applied during this period.

As will be described in detail in the following Examples, the novel compound of the present invention functions as a strong sex attractant for drugstore beetles. Therefore, adult male drugstore beetles can be attracted and exterminated at a single location or normal mating behavior of adult male drugstore beetles can be artificially disturbed. Furthermore, when this sex attractant is used to attract and exterminate drugstore beetles to determine the occurrence of drugstore beetles, the need and timing for application of the sex attractant can be determined and the amount of the insecticide used can be minimized.

EXAMPLE 1

Isolation of Stegobiol

About 100,000 adult drugstore beetles including 50,000 adult females grown with a culturing medium and within 4 to 6 days from emergence were subject to extraction with about 2,000 ml of hexane for 24 hours, and the extract was filtered. The filtrate was concentrated under reduced pressure to provide 5 g of a concentrate. The concentrate was subjected to column chromatography using 100 g of silica gel (available from Merck & Co., Inc.) which was about 20 times in amount that of the concentrate. More specifically, after dissolving 5 g of the concentrate in 5 ml of hexane, it was allowed to be adsorbed in the silica gel column and was sequentially allowed to elute in 250 ml of each of hexane, a hexane/ethyl ether (90:10; volume ratio) mixture, a hexane/ethyl ether (80:20) mixture, a hexane/ethyl ether (70:30) mixture, a hexane/ethyl ether (50:50) mixture solution, and ethyl ether. The eluted fractions in ethyl ether were concentrated at a reduced pressure at 30° to 50° C. to provide 10 mg of the concentrate.

The resultant concentrate was subjected to high-performance chromatography using a Zorbax sil column (4.6 mm×25 cm; available from du Pont de Nemours). Using a hexane/tetrahydrofuran (85:15) mixture as a mobile phase, a peak fraction appearing on a retention time of 12 minutes (flow rate: 2.0 ml/min) was sampled by detection at an absorption wavelength of UV 270 nm), thereby obtaining 2 mg of stegobiol.

The obtained stegobiol was a colorless liquid. The data of the mass spectrometry, and proton and carbon NMR specra of the stegobiol are presented below:
High-Resolution Mass Spectrum)
$C_{13}H_{22}O_3$: Found 226.1535; Calculated 226.1567.
Mass Spectrum (70 eV) m/z (%): 226 (M+, 8), 168(88), 141(20), 139(17), 124(15), 113(70), 112(100), 109(27), 101(17), 85(17), 84(15), 83(87), 70(16), 59(49), 57(33), 56(37), 55(45), 43(41), 41(52).
Proton NMR spectrum (500 MHz), ppm, numbers in parentheses represent the proton number, ramification, and configuration. The atom numbers used in indicating the configuration are defined as follows:

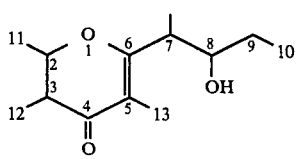

1.00 (3H, t, J=7.4 Hz, Me-10)
1.04 (3H, d, J=7.3 Hz, Me-12)
1.18 (3H, d, J=7.1 Hz, Me-14)
1.33 (3H, d, J=6.6 Hz, Me-11)
1.42 (1H, m, H-9)
1.60 (1H, m, H-9')
1.75 (1H, s, Me-13)
1.89 (1H, d, J=7.4 Hz)
2.38 (1H, dq, J=7.3, 3.4 Hz, H-3)
2.86 (1H, dq, J=7.1, 6.8 Hz, H-7)
3.58 (1H, m, H-8)
4.49 (1H, dq, J=6.6, 3.4 Hz, H-2) $^{13}$C-NMR spectrum (125 MHz), ppm
197.1, 172.7, 109.5, 75.5, 43.8, 40.9, 28.3, 15.9, 14.8, 10.1, 9.4, 9.3

EXAMPLE 2

Synthesis of Stegobiol 22.6 g (0.1 moles) of 2,3-dihydro-2,3,5-trimethyl-6-(1-methyl-2-oxobutyl)-4H-pyran-4-one(stegobinone) prepared in accordance with the amended Examples 1 and 2 described in Japanese Patent Disclosure No. 59-112981 were dissolved in 100 ml of ethyl ether. 3.8 g (0.1 moles) of sodium borohydride and 10.1 g of zinc chloride (0.1 moles) were added to the solution, and the solution was agitated at room temperature for 3 hours. The reaction solution was poured into 300 ml of ice water and 200 ml of ethyl ether, strongly agitated and washed with water. The ethyl ether phase was concentrated at a reduced pressure to provide 22 g of the reaction mixture. The reaction mixture was fractionated by silica gel column chromatography by the method described in Example 1 to obtain 14.3 g of stegobiol. The compound prepared in this Example was determined to consist of a stereoisomer mixture (i.e., diasteroisomer) by gas chromatography (Carbowax 20 M, 25 m, 100° C–210° C., 210° C./min). Each isomer had a mass spectrum which coincided with one indicated in Example 1.

EXAMPLE 3

A mixture consisting of 16.8 g (0.1 moles) of 2,3-dihydro-2,3,5-trimethyl-6-ethyl-4H-pyran-4-on, 12.2 g (0.12 moles) of acetic anhydride, and 10.7 g (0.075 moles) of boron trifluoride was cooled on an ice bath. 26.5 g (0.25 moles) of methyl orthoformate were added dropwise to the mixture. Thereafter, the reaction mixture was allowed to react at 20° to 25° C. for 3 hours to obtain 20.6 g of 2,3,5-trimethyl-6-(2-methyl-1,1-dimethoxyethyl)-4H-pyran-4-one. The yield was 85%.
Analysis Results
Boiling point: 93° to 96° C./0.6 mmHg.
Mass spectrum (70 eV) m/z (%): 211(4), 210(2), 179(2), 111(9), 99(29), 83(31), 75(100), 72(7), 56(7), 55(10), 47(19), 41(15).
Infrared spectrum $\nu$max (cm$^{-1}$): 1665, 1610.

EXAMPLE 4

22.1 g of 2,3-dihydro-2,3,5-trimethyl-6-(2-methyl-1,1-diethoxyethyl)-4H-pyran-4-one were prepared following the same procedures as in Example 1 except that 37 g (0.25 moles) of ethyl orthoformate were used in place of methyl orthoformate. The yield was 82%.
Analysis Results
Boiling point: 98° to 102° C./0.6 mmHg.
Mass analysis spectrum (70 eV) m/z (%): 225(5), 224(10), 179(9), 141(7), 125(7), 124(6), 113(61), 103(100), 85(35), 83(42), 47(69), 43(31).
Infrared spectrum $\nu$max (cm$^{-1}$): 1665, 1610.

EXAMPLE 5

12.1 g (0.05 moles) of 2,3-dihydro-2,3,5-trimethyl-6-(2-methyl-1,1-dimethoxyethyl)-4H-pyran-4-on obtained in Example 1 were mixed with 20 ml of a 5% hydrochloric acid solution and 40 ml of acetonitrile. The mixture was agitated on a water bath at 40° to 45° C. for 5 hours to obtain 22.1 g of 2,3-dihydro-2,3,5-trimethyl-6-(2-methyl-1-oxoethyl)-4H-pyran-4-one. The yield was 94%.

Analysis Results

Mass spectrum (70 eV) m/z (%): 168(45), 113(100), 83(52).

Infrared spectrum $\nu$max (cm$^{-1}$): 1730, 1664, 1611.

EXAMPLE 6

After dissolving 6.8 g (0.05 moles) of zinc chloride in 120 ml of dehydrated tetrahydrofuran, 3.8 g (0.1 moles) of sodium borohydride were added to the solution. The mixture was agitated at 40° C. for 1 hour. After the mixture was cooled with ice, 9.8 g (0.05 moles) of 2,3-dihydro-2,3,5-trimethyl-6-(2-methyl-1-oxoethyl)-4H-pyran-4-one were dripped. After agitating the mixture for 3 hours, 8.7 g of 2,3-dihydro-2,3,5-trimethyl-6-(2-methyl-1-hydroxyethyl)-4H-pyran-4-one were obtained. The yield was 88%.

Analysis Results

Mass spectrum (70 eV) m/z (%): 198(M,27), 143(40), 100(33), 87(31), 83(100), 59(31), 56(28), 55(25), 42(22), 41(38).

Infrared spectrum $\nu$max (cm$^{-1}$): 3400, 1660, 1605.

EXAMPLE 7

40.4 g (0.1 moles) of methyltriphenylphosphonium iodide were suspended in 400 ml of anhydrous ether under argon gas flow. After cooling the mixture to 0° C., 90 ml (0.15 moles) of a hexane solution of n-butyl lithium were dripped. 19.6 g (0.1 moles) of 2,3-dihydro-2,3,5-trimethyl-6-(2-methyl-1-oxoethyl)-4H-pyran-4-on obtained in Example 3 were added dripwise to the mixture solution, and the mixture was agitated for 1 hour to obtain 10.1 g of 2,3-dihydro-2,3,5-trimethyl-6-(3-methyl-1-propenyl)-4H-pyran-4-one. The yield was 56%.

Analysis Results

Mass analysis spectrum (70 eV) m/z (%): 194(12), 139(29), 83(100).

Infrared spectrum $\nu$max (cm$^{-1}$): 1730, 1665, 1610.

EXAMPLE 8

An ethyl ether solution of 13.8 g (0.05 moles) of 2,3-dihydro-2,3,5-trimethyl-6-(2-methyl-2-bromo-1-oxoethyl)-4H-pyran-4-one was dripped to ethylmagnesium bromide prepared from 1.5 g of magnesium and 6.6 g of ethyl bromide in 200 ml of ethyl ether. After the ether solution was agitated at room temperature for 1 hour, 1.2 g (0.05 moles) of magnesium were added and the mixture was agitated for 3 more hours. The reaction mixture was poured into 100 ml of dilute hydrochloric acid to concentrate the ether layer, thereby providing 7.9 g of 2,3-dihydro-2,3,5-trimethyl-6-(1-methyl-1-butenyl)-4H-pyran-4-one. The yield was 79%.

Analysis Results

Mass spectrum (70 eV) m/z (%): 208(46), 179(96), 153(28), 137(33), 97(100).

Infrared spectrum $\nu$max (cm$^{-1}$): 3457, 1660, 1600.

EXAMPLE 9

10.6 g of 2,3-dihydro-2,3,5-trimethyl-6-(1-methyl-2-butenyl)-4H-pyran-4-one were prepared following the same procedures as in Example 5 except that 41.8 g (0.1 moles) of ethyltriphenylphosphonium iodide were used in place of methyltriphenylphosphonium iodide. The yield was 51%.

Analysis Results

Mass spectrum (70 eV) m/z (%): 208(19), 153(29), 83(100).

Infrared spectrum $\nu$max (cm$^{-1}$): 1665, 1610.

EXAMPLE 10

After adding 7.9 g (0.1 moles) of pyridine and 7.8 g (0.1 moles) of acetyl chloride to 100 ml of dehydrated dimethylformamide and cooling the mixture with ice, 11.3 g (0.05 moles) of stegobiol were dripped and agitated at 20° at 25° C. for 10 hours to provide 12.1 g of 2,3-dihydro-2,3,5-trimethyl-6-(1-methyl-1-acetoxyethyl)-4H-pyran-4-on. The yield was 90%.

Analysis Results

Mass spectrum (70 eV) m/z (%); 268(M,1), 208(5), 179(43), 168(63), 153(38), 152(23), 124(19), 113(15), 101(20), 83(60), 55(17), 43(100).

Infrared spectrum $\nu$max (cm$^{-1}$): 1735, 1665, 1610.

EXAMPLE 11

Sex Attraction Effect of Stegobiol

Paper filter having a size of 1.5 cm×0.5 cm (No. 5 available from Toyo Roshi K.K.) were folded in three layers to provide screens. Stegobiol was dissolved in amounts of hexanes indicated as Nos. 1 to 10 in Table 1 below to obtain solutions in total amounts of 1 $\mu$l, respectively. Each solution was added to one screen with a syringe. The stegobiol used was the one prepared by the method described in Example 1.

Ten non-copulated adult male drugstore beetles within 4 to 6 days from emergence were put into a petri dish having a diameter of 10 cm. The paper filter wetted with the stegobiol was placed in the petri dish. As a control, a similar paper filter wetted with 1 $\mu$l of hexane alone was placed in another petri dish, and 10 similar adult male drugstore beetles were also put into the control petri dish. When the sex attraction effects in the petri dishes were examined, the results as shown in Table 1 were obtained. The experiment was repeated three times for each solution, and an average value obtained by the three experiments is indicated.

TABLE 1

| Sample No. | Stegobiol Weight ($\mu$g) | A*1 | B*2 |
| --- | --- | --- | --- |
| 1 | 20 | 10 | 0 |
| 2 | 10 | 10 | 0 |
| 3 | 1 | 10 | 0 |
| 4 | $1 \times 10^{-1}$ | 10 | 0 |
| 5 | $1 \times 10^{-2}$ | 10 | 0 |
| 6 | $1 \times 10^{-3}$ | 10 | 0 |
| 7 | $1 \times 10^{-4}$ | 10 | 0 |
| 8 | $1 \times 10^{-5}$ | 8 | 0 |
| 9 | $1 \times 10^{-6}$ | 5 | 0 |
| 10 | $1 \times 10^{-7}$ | 1 | 0 |

*1: The number of male drugstore beetles collected at the filter paper wetted with the stegobiol.
*2: The number of male drugstore beetles collected at the filter paper wetted with hexane alone.

EXAMPLE 12

A comparison between stegobiol and stegobinone in respect of the sex attraction effect will be made below.

A paper filter having a diameter of 9 cm was placed in a petri dish having the same diameter. Ten non-copulated adult male drugstore beetles were put on the paper filter and the dish was placed at a bright location at 28° C. and 60% humidity. A paper filter piece having a size of 5 mm×2 cm was folded, stegobiol or stegobinone was added to the folded filter, and the filter was placed in a petri dish. The amount of stegobiol or stegobinone added was 10 to $10^{-5}$ μg. The stegobiol and stegobinone were those extracted from female drugstore beetles. The total number of male drugstore beetles attracted to each paper filter in 10 minutes was counted. The experiment was repeated five times, and an average value is indicatd in Table 2.

TABLE 2

| Addition Amount (μg) | Stegobiol | Stegobinone |
|---|---|---|
| $1 \times 10^{-5}$ | 8.17* | 10.33 |
| $1 \times 10^{-3}$ | 11.71 | 4.60 |
| $1 \times 10^{-2}$ | 32.86 | 4.67 |
| $1 \times 10^{-1}$ | 61.17 | 6.43 |
| 1 | 58.17 | 0.57 |
| 10 | 68.00 | 3.80 |

*Total number of attracted worms

EXAMPLE 13

The same test was conducted as in Example 11 except that 1 μg of each of the compounds obtained in Example 3 to 10 was used instead of stegobiol. Results are shown in Table 3 below.

TABLE 3

| Compound Example No. | A*1 | B*2 |
|---|---|---|
| 3 | 10 | 0 |
| 4 | 10 | 0 |
| 5 | 10 | 0 |
| 6 | 10 | 0 |
| 7 | 10 | 0 |
| 8 | 10 | 0 |
| 9 | 10 | 0 |
| 10 | 10 | 0 |

*1: The number of male drugstore beetles collected at the filter paper treated with the compound.
*2: The number of male drugstore beetles collected at the filter paper wetted with hexane alone.

EXAMPLE 14

Polypropylene disks having a diameter of 1 cm and a thickness of 3 mm and coated with the compounds of Examples 3 to 10 were placed on central portions of adhesive plates having a size of 6 cm×15 cm to prepare samples. Likewise, similar polypropylene disks without coatings were placed on similar adhesive plates to prepare controls.

Each of the samples was placed in a rectangular room of 20 m3 together with the control. The sample was separated from the control by 2 m. Thirty adult male drugstore beetles were put into the room at a temperature of 28° C. and a humidity of 60% for 2 days. The number of the worms held on the adhesive plate was counted. The same tests were also conducted on stegobiol and stegobinone. Results are shown in Table 4 below.

TABLE 4

| Compounds Example No. | Sample | Control |
|---|---|---|
| 1 | 25 | 0 |
| 2 | 20 | 0 |
| 3 | 12 | 0 |
| 4 | 12 | 0 |
| 5 | 17 | 0 |
| 6 | 24 | 0 |
| 7 | 22 | 0 |
| 8 | 13 | 0 |
| Stegobiol | 7 | 0 |
| Stegobinone | 0 | 0 |

What is claimed is:

1. A 2,3-dihydro-2,3,5-trimethyl-4H-pyran-4-one derivative represented by general formula:

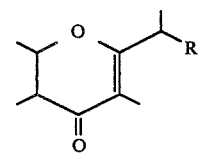

where R is —CH(OCH$_3$)$_2$, —CH(OC$_2$H$_5$)$_2$, —CHO, —CH$_2$OH, —CH=CH$_2$, =CHCH$_2$CH$_3$, —CH=CHCH$_3$ or

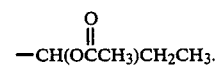
—CH(OCCH$_3$)CH$_2$CH$_3$.

2. The derivative of claim 1, wherein said R is —CH(OCH3)$_2$.
3. The derivative of claim 1, wherein said R is —CH(OC2H5)$_2$.
4. The derivative of claim 1, wherein said R is —CHO.
5. The derivative of claim 1, wherein said R is —CH$_2$
6. The derivative of claim 1, wherein said R is —CH=CH$_2$.
7. The derivative of claim 1, wherein said R is =CHCH$_2$CH$_3$.
8. The derivative of claim 1, wherein said R is —CH=CHCH$_3$.
9. The derivative of claim 1, wherein said R is

—CH(OCCH$_3$)CH$_2$CH$_3$.

10. A 2,3-dihydro-2,3,5-trimethyl-4H-pyran-4-one compound in substantially pure form, said compound being represented by the formula:

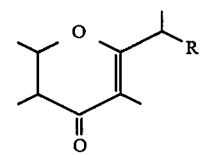

where R is

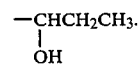
—CHCH$_2$CH$_3$.
  |
  OH

* * * * *